(12) United States Patent
Chen et al.

(10) Patent No.: US 9,810,667 B2
(45) Date of Patent: Nov. 7, 2017

(54) HEEL TEST BLOCK

(71) Applicant: NANJING DEVELOP ADVANCED MANUFACTURING CO., LTD., Nanjing, Jiangsu (CN)

(72) Inventors: Changhua Chen, Jiangsu (CN); Li Zhang, Jiangsu (CN); Xiaolei Liu, Jiangsu (CN); Yao Ha, Jiangsu (CN); Zhengmao Xu, Jiangsu (CN); Zheng Dong, Jiangsu (CN); Qingyong Chen, Jiangsu (CN)

(73) Assignee: Nanjing Develop Advanced Manufacturing Co., Ltd., Nanjing, Jiangsu (CN)

( * ) Notice: Subject to any disclaimer, the term of this patent is extended or adjusted under 35 U.S.C. 154(b) by 58 days.

(21) Appl. No.: 14/436,688

(22) PCT Filed: Jul. 9, 2014

(86) PCT No.: PCT/CN2014/081864
§ 371 (c)(1),
(2) Date: Apr. 17, 2015

(87) PCT Pub. No.: WO2015/161568
PCT Pub. Date: Oct. 29, 2015

(65) Prior Publication Data
US 2016/0231292 A1    Aug. 11, 2016

(30) Foreign Application Priority Data

Apr. 23, 2014  (CN) .......................... 2014 1 0166754

(51) Int. Cl.
*G01N 29/30* (2006.01)
(52) U.S. Cl.
CPC .................................. *G01N 29/30* (2013.01)

(58) Field of Classification Search
CPC ........... G01N 29/30; G01D 18/00; G01B 3/56
(Continued)

(56) References Cited

U.S. PATENT DOCUMENTS 3,933,026 A * 1/1976 Ham .................. G01N 29/4463
73/1.86
4,173,139 A * 11/1979 Conn ................. G01N 29/4463
73/1.84
(Continued)

FOREIGN PATENT DOCUMENTS

CN          101078710         11/2007
CN          103217484          7/2013
(Continued)

OTHER PUBLICATIONS

International Search Report filed in PCT/CN2014/081864.

*Primary Examiner* — Natalie Huls
(74) *Attorney, Agent, or Firm* — Rankin, Hill & Clark LLP

(57) ABSTRACT

A heel test block comprises a semi-cylinder, a first flat plate and a second flat plate, wherein the side surface of the semi-cylinder comprises a circular arc-shaped surface and a first plane, the first flat plate and the second flat plate are arranged on one side of the first plane, all the parts of the first flat plate have the same thickness, all the parts of the second flat plate have the same thickness, the first flat plate and the second flat plate are arranged in parallel to the first plane, the first flat plate and the second flat plate are arranged on the two sides of the mother line of the semi-cylinder respectively, and the thickness of the first flat plate is less than that of the second flat plate.

9 Claims, 2 Drawing Sheets

(58) Field of Classification Search
USPC .......................................................... 73/1.81
See application file for complete search history.

(56) References Cited

U.S. PATENT DOCUMENTS

| | | | | |
|---|---|---|---|---|
| 5,163,027 A | * | 11/1992 | Miller | G01B 3/30 367/13 |
| 5,665,893 A | * | 9/1997 | Smith | G01N 29/30 73/1.82 |
| 5,837,880 A | * | 11/1998 | Shakinovsky | G01N 29/223 73/1.86 |
| 6,415,644 B1 | * | 7/2002 | Rockwood | G01B 17/02 73/1.86 |
| 6,938,457 B2 | * | 9/2005 | Johnson | G01N 29/2487 33/534 |
| 2012/0130653 A1 | * | 5/2012 | Zhang | G01N 29/069 702/56 |
| 2013/0180312 A1 | * | 7/2013 | Jones | G01N 29/262 73/1.82 |
| 2016/0069843 A1 | * | 3/2016 | Buechner | G01N 29/30 73/1.86 |

FOREIGN PATENT DOCUMENTS

| | | |
|---|---|---|
| CN | 103454349 | 12/2013 |
| EP | 1522848 | 4/2005 |

\* cited by examiner

HEEL TEST BLOCK

FIELD OF THE INVENTION

The invention belongs to the field of precision positioning of horizontality, verticality and sound paths for oblique incidence ultrasonic flaw detection of hollow forged pieces in the direction of circumferential surfaces.

BACKGROUND OF THE INVENTION

At present, main standard test blocks for calibration work of ultrasonic flaw detectors and probes mainly comprise V1 (IIW1) boat-shaped test blocks and V2 (IIW2) ox horn test blocks, which are mainly used for the detection of horizontal linearity, vertical linearity, dynamic range, sensitivity margin, differentiating force and blind areas, as well as incidence points, refraction angles and the like of the probes, and the detection surfaces of the probes are planes. Heel test blocks have the functions which are basically the same as those of the boast-shaped test blocks or the ox horn test blocks, but the detection surfaces of the probes are curved surfaces. The surfaces of workpieces are generally planes and curved surfaces, when the planes are used as the detection surfaces for performing flaw detection work, the boat-shaped test blocks and the ox horn test blocks are used for calibration of the instruments and the probes; and when the curved surfaces are used as the detection surfaces for performing the flaw detection work, there are no detection test blocks worldwide for the calibration of the instruments and the probes.

There have been no standard test blocks for debugging internationally for precision positioning of ultrasonic circumferential oblique defect detection of curved surface forged pieces. How to determine detection angle, scanning speed and zero point of each curved surface forged piece becomes an important difficult problem in the field of nondestructive detection. For the circumferential oblique defect detection of the parts of oil and gas drilling and production equipment, an internationally adopted flaw detection method is mainly as follows: a line is connected between peak values of a first reflex obtained on a notch between the inner diameter and the outer diameter to establish a datum line of vibration amplitude. But, the precision positioning of defects can not be ensued, and the existing contrast test blocks can not meet the calibration work of the angles, the speeds and the zero points.

Thus, a new contrast test block is needed to solve the above problems.

SUMMARY OF THE INVENTION

The invention aims at providing a heel test block which can calibrate the angle, sound speed and zero point of a curved surface forged piece subjected to circumferential oblique detection against the defect that contrast test blocks in the prior art can not meet the calibration of angles, scanning speeds and zero points.

The technical scheme is as follows: in order to solve the above technical problem, the heel test block of the invention adopts the following technical scheme:

A heel test block comprises a semi-cylinder, a first flat plate and a second flat plate, wherein the side surface of the semi-cylinder comprises a circular arc-shaped surface and a first plane, the first flat plate and the second flat plate are arranged on one side of the first plane, all the parts of the first flat plate have the same thickness, all the parts of the second flat plate have the same thickness, the first flat plate and the second flat plate are arranged in parallel to the first plane, the first flat plate and the second flat plate are arranged on the two sides of the mother line of the semi-cylinder respectively, and the thickness of the first flat plate is less than that of the second flat plate.

Further, the heel test block also comprises a third flat plate, wherein all the parts of the third flat plate have the same thickness, the third flat plate is arranged in parallel to the first flat plate, a gap exists between the third flat plate and the first flat plate, and the thickness sum of the first flat plate, the third flat plate and the gap is equivalent to the thickness of the second flat plate. The design can ensure that the plane of the third flat plate, which is far away from the semi-cylinder, is flush with the plane of the first flat plate, which is far away from the semi-cylinder, thereby facilitating the placement of the heel test block.

Further, the thickness of the gap is 5 mm±0.5 mm.

Further, the thickness of the first flat plate is 30 mm±0.1 mm and the thickness of the second flat plate is 60 mm±0.1 mm. The maximum size of a search unit of a common oblique probe is 13×13 mm$^2$, and the frequency of the probe is 2.5 MHz, so that $\lambda=C/f=(3230\times10^3)/(2.5\times10^6)=1.29$ mm. As the sound path between the probe and a reflection hole must be greater than 2 times the distance of a near-field region of the probe during the angle measurement of the probe, the errors of measurement results caused by the influence of the near-field region can be avoided and $N \geq d^2/(4\times\lambda)=13^2/(4\times1.29)=32.8$ mm must be met. Furthermore, because the radius R of a circular arc is generally greater than 30 mm, the spacing interval between a rectangular groove of the gap and the center of a semi-circular arc is 30 mm, which can meet the lowest requirements on the angle measurement errors of the probe. The distance between the center of the semi-circular arc and the side of 2R length of a cuboid is 60 mm, which is 2 times of 30 mm which is considered, namely the condition of being greater than 2N is met.

Further, the length of the semi-cylinder and the width of the first flat plate are equivalent to the width of the second flat plate. The same thickness of all the parts of the heel test block is further ensured.

Further, the upper surface and the lower surfaces of the semi-cylinder are planes, and angle scales are arranged on the upper surface and/or the lower surface. By arranging the angle scales, the incidence angle of the oblique probe can be conveniently detected.

Further, the first flat plate and the second flat plate are cuboids.

Further, the radius of the semi-cylinder is R, and the length of each of the first flat plate and the second flat plate is R.

Further, the length of the semi-cylinder, the width of the first flat plate and the width of the second flat plate are not less than 25 mm.

The heel test block has the beneficial effects that the heel test block of the invention has a simple structure, and can calibrate the angle, the sound speed and the zero point for circumferential oblique probing of the curved surface forged piece, and by utilizing the proportion of an instrument calibrated by the heel contrast test block of the invention, the purpose of accurate calibration of the instrument is fulfilled, thereby being more conductive to ultrasonic defect positioning and flaw detection of the curved surface forged pieces.

DETAILED DESCRIPTION OF THE EMBODIMENTS

The invention is further described in detail in conjunction with the following accompanying drawings and specific embodiments.

Figure 1:
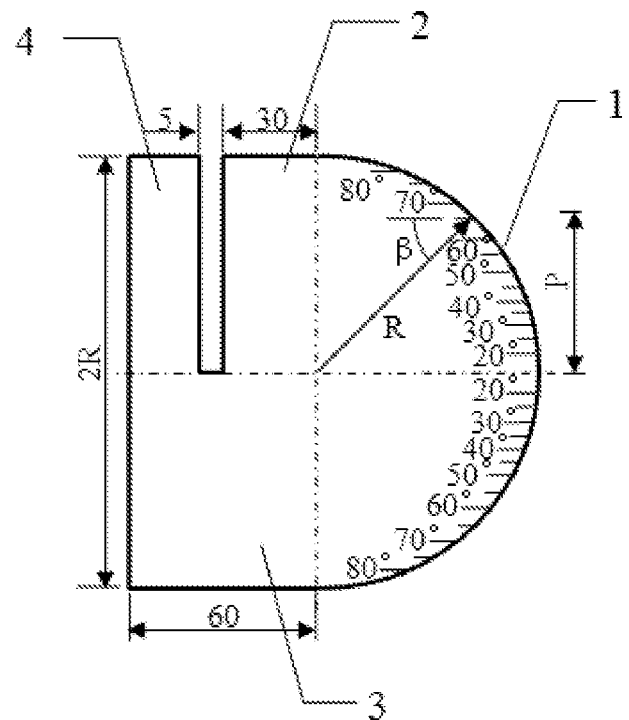
FIG. 1 is a main view of a heel test block of the invention.
Figure 2:
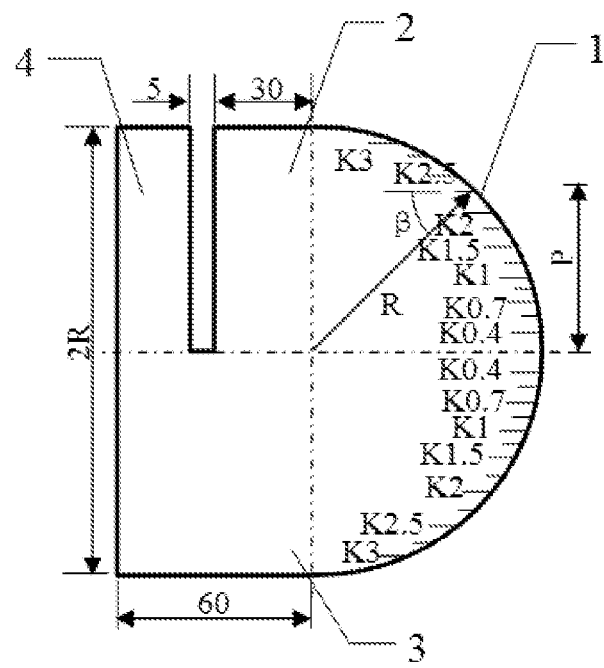
FIG. 2 is a rear view of the heel test block of the invention.
Figure 3:
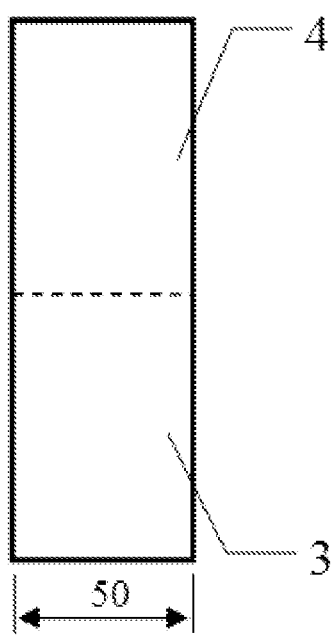
FIG. 3 is a left view of the heel test block of the invention.

As shown in FIG. 1, FIG. 2 and FIG. 3, a heel test block of the invention comprises a semi-cylinder 1, a first flat plate 2 and a second flat plate 3, wherein the side surface of the semi-cylinder 1 comprises a circular arc-shaped surface and a first plane, the first flat plate 2 and the second flat plate 3 are arranged on one side of the first plane, all the parts of the first flat plate 2 have the same thickness, and all the parts of the second flat plate 3 have the same thickness. The first flat plate 2 and the second flat plate 3 are arranged in parallel to the first plane, the first flat plate 2 and the second flat plate 3 are arranged on the two sides of the mother line of the semi-cylinder 1 respectively. The thickness of the first flat plate 2 is less than that of the second flat plate 3.

The heel test block further comprises a third flat plate 4, wherein all the parts of the third flat plate 4 have the same thickness, the third flat plate 4 is arranged in parallel to the first flat plate 2, a gap exists between the third flat plate 4 and the first flat plate 2, and the thickness sum of the first flat plate 2, the third flat plate 4 and the gap is equivalent to the thickness of the second flat plate 3. The design can ensure that the plane of the third flat plate, which is far away from the semi-cylinder, is flush with the plane of the first flat plate, which is far away from the semi-cylinder, thereby facilitating the placement of the heel test block. Wherein, the distance between the first flat plate 2 and the third flat plate 4 is 5 mm.

Wherein, the flat plate 2 and the second flat plate 3 are cuboids, and the upper surface and the lower surface of the semi-cylinder 1 are planes, the point of the circular arc-shaped surface, which is far away from the first plane, is the top of the heel test block;

the plane of the second flat plate 3, which is far away from the semi-cylinder 1, is the bottom of the heel test block;

the distance between the plane of the second flat plate 3, which is far away from the semi-cylinder 1, and the point of the circular arc-shaped surface of the semi-cylinder 1, which is far away from the first plane, is the height of the heel test block;

the distance between the upper surface and the lower surface of the semi-cylinder 1 is the thickness of the heel test block;

the distance between line segments of the plane of the semi-cylinder 1, which are connected with the circular arc-shaped surface, is the width of the heel test block, and the width of the heel test block is twice the radius of the semi-cylinder 1;

the distance between the upper surface and the lower surface of the semi-cylinder 1 is the height of the semi-cylinder 1;

the distance between the plane of the first flat plate 2, which is near the second flat plate 3, and the plane of the first flat plate 2, which is far away from the second flat plate 3, is the length of the first flat plate 2;

the distance between the plane of the second flat plate 3, which is near the first flat plate 2, and the plane of the second flat plate 3, which is far away from the first flat plate 2, is the length of the second flat plate 3;

the distance between the plane of the second flat plate 3, which is far away from the semi-cylinder 1, and the plane of the semi-cylinder 1 is the thickness of the second flat plate 3;

the distance between the plane of the first flat plate 2, which is far away from the semi-cylinder 1, and the plane of the semi-cylinder 1 is the thickness of the first flat plate 2;

the distance between the first flat plate 2 and the two planes corresponding the upper surface and the lower surface of the semi-cylinder 1 is the width of the first flat plate 2; and the distance between the second flat plate 3 and the two planes corresponding the upper surface and the lower surface of the semi-cylinder 1 is the width of the second flat plate 3.

The length of the semi-cylinder 1 and the width of the first flat plate 2 are equivalent to the width of the second flat plate 3. Angle scales are arranged on the upper surface and/or lower surface. By arranging the angle scales, the incidence angle of an oblique probe can be conveniently detected. The surfaces with the scales of the semi-cylinder are chamfered by R2=0.5±0.1 mm and the surfaces without the scales are chamfered by R1=1±0.1 mm. The planeness of the surface of the first flat plate 2, which is far away from the semi-cylinder 1, is less than 0.05 mm, the planeness of the two opposite surfaces is less than 0.05 mm, the planeness of the surface of the second flat plate 3, which is far away from the semi-cylinder 1, is less than 0.05 mm, and the planeness of the two opposite surfaces is less than 0.05 mm.

The radius of the semi-cylinder 1 is R, and the length of each of the first flat plate 2 and the second flat plate 3 is R. The radius R of the semi-cylinder 1 has the tolerance of ±0.1 mm. The length of the semi-cylinder 1, the width of the first flat plate 2 and the width of the second flat plate 3 are not less than 25 mm. Preferably, the length of the semi-cylinder 1, the width of the first flat plate 2 and the width of the second flat plate 3 are 50±0.10 mm.

The thickness of the first flat plate 2 is 30 mm±0.1 mm and the thickness of the second flat plate 3 is 60 mm±0.1 mm. The maximum size of a search unit of the common oblique probe is 13×13 mm$^2$, and the frequency of the probe is 2.5 MHz, so that $\lambda=C/f=(3230\times10^3)/(2.5\times10^6)=1.29$ mm. As the sound path between the probe and a reflection hole must be greater than 2 times the distance of a near-field region of the probe during the angle measurement of the probe, the errors of measurement results caused by the influence of the near-field region can be avoided and $N\geq d^2/(4\times\lambda)=13^2/(4\times1.29)=32.8$ mm must be met. Furthermore, because the radius R of a circular arc is generally greater than 30 mm, the spacing interval between a rectangular groove of the gap and the center of a semi-circular arc is 30 mm, which can meet the lowest requirements on the angle measurement errors of the probe. The thickness of the second flat plate 2 is 60 mm, which is 2 times of 30 mm which is considered, namely the condition of being greater than 2N is met.

Embodiment 1

A contrast test block for calibration angle, sound speed and zero point of a curved surface forged piece is called as a heel test block, the thickness of the heel test block is 2" (50 mm), the width is 2R and the height is R+60. The calculation formula of the positions P of angle long scales on the upper surface and/or the lower surface of a semi-cylinder is as follows: P=R×Sin (β), wherein β is 20°, 30°, 40°, 50°, 60°, 70° or 80°. The calculation method of the positions P of angle short scales is the same as that of the angle long scales, the short scales are 25°, 35°, 45°, 55°, 65° and 75° respectively and the parameters of the positions P of the angle scales are as show in Table 1.

TABLE 1

Fabrication parameters of positions of angle scales on semi-circular side surface

| Serial number | Type of test block | R radius | 20° P position | 30° P position | 40° P position | 50° P position | 60° P position | 70° P position | 80° P position |
|---|---|---|---|---|---|---|---|---|---|
| 1 | 4130-AVZ-0197 CHB50 | 50 | 17.1 | 25 | 32.1 | 38.3 | 43.3 | 47.0 | 49.2 |
| 2 | 4130-AVZ-0394 CHB100 | 100 | 34.2 | 50 | 64.3 | 76.6 | 86.6 | 94.0 | 98.5 |
| 3 | 4130-AVZ-0591 CHB150 | 150 | 51.3 | 75 | 96.4 | 114.9 | 129.9 | 141.0 | 147.7 |
| 4 | 4130-AVZ-0787 CHB200 | 200 | 68.4 | 100 | 128.6 | 153.2 | 173.2 | 187.9 | 197.0 |
| 5 | 4130-AVZ-0984 CHB250 | 250 | 85.5 | 125 | 160.7 | 191.5 | 216.5 | 234.9 | 246.2 |
| 6 | 4130-AVZ-1181 CHB300 | 300 | 102.6 | 150 | 192.8 | 229.8 | 259.8 | 281.9 | 295.4 |
| 7 | 4130-AVZ-1378 CHB350 | 350 | 119.7 | 175 | 225.0 | 268.1 | 303.1 | 328.9 | 344.7 |
| 8 | 4130-AVZ-1575 CHB400 | 400 | 136.8 | 200 | 257.1 | 306.4 | 346.4 | 375.9 | 393.9 |

Note:
the length unit is mm.

The roughness Ra≤6.3 um and a raw material warranty certificate, a forging process, heat treatment parameters, inspection records of processing sizes and the like should be complete. The parameters of the test blocks are as shown in Table 2.

TABLE 2

Fabrication parameters of contrast test blocks

| Serial number | Type of test block | R radius mm | W width mm | H height mm |
|---|---|---|---|---|
| 1 | 4130-AVZ-0197 CHB50 | 50 | 100 | 110 |
| 2 | 4130-AVZ-0394 CHB100 | 100 | 200 | 160 |
| 3 | 4130-AVZ-0591 CHB150 | 150 | 300 | 210 |
| 4 | 4130-AVZ-0787 CHB200 | 200 | 400 | 260 |
| 5 | 4130-AVZ-0984 CHB250 | 250 | 500 | 310 |
| 6 | 4130-AVZ-1181 CHB300 | 300 | 600 | 360 |
| 7 | 4130-AVZ-1378 CHB350 | 350 | 700 | 410 |
| 8 | 4130-AVZ-1575 CHB400 | 400 | 800 | 460 |

Note:
the fabrication requirements are as follows:
R—semi-circle, and the tolerance is ±0.015″(0.38 mm);
W—width, the tolerance is ±0.030″ (0.76 mm);
H—height, the tolerance is ±0.030″ (0.76 mm);
P-angle position line, the tolerance is ±0.001″ (0.25 mm);
I-typical test block mark;
4130 = typical alloy grade;
K = tangent value of angle,
V = sound speed and
Z = zero point;
0118 = 01.18″, metal radius, and the unit is 00.00″;
CHB = heel test block; and
tri-position: 456 = radius of outer circle 456 mm.

Embodiment 2

A contrast test block for calibration K value, sound speed and zero point of a curved surface forged piece is called as a heel test block, the thickness of the heel test block is 25 mm, the width is 2R and the height is R+60. The calculation formula of positions P of K value long scales of a semi-circular side surface is as follows: P=R×Sin (β), wherein K=Tan (β), which is 0.4, 0.7, 1.0, 1.5, 2.0, 2.5 or 3.0. The calculation method of the positions P of K value short scales is the same as that of the K value long scales, the short scales K are 0.55, 0.85, 1.25, 1.75, 2.25 and 2.75 respectively and the parameters of the positions P of the K value scales are as show in Table 3.

TABLE 3

Fabrication parameters of positions of K value scales on semi-circular side surface

| Serial number | Type of test block | R radius | K0.4 P position | K0.7 P position | K1.0 P position | K1.5 P position | K2.0 P position | K2.5 P position | K3.0 P position |
|---|---|---|---|---|---|---|---|---|---|
| 1 | 45-KVZ-0394 CHB100 | 100 | 37.1 | 57.3 | 70.7 | 83.2 | 89.4 | 92.9 | 94.9 |

Note:
the length unit is mm.

The roughness Ra≤6.3 um and a raw material warranty certificate, a forging process, heat treatment parameters, inspection records of processing sizes and the like should be complete. The parameters of the test blocks are as shown in Table 4.

TABLE 4

Fabrication parameters of contrast test blocks

| Serial number | Type of test block | R radius mm | W width mm | H height mm |
|---|---|---|---|---|
| 1 | 4130-KVZ-0197 CHB50 | 50 | 100 | 110 |
| 2 | 4130-KVZ-0394 CHB100 | 100 | 200 | 160 |
| 3 | 4130-KVZ-0591 CHB150 | 150 | 300 | 210 |
| 4 | 4130-KVZ-0787 CHB200 | 200 | 400 | 260 |
| 5 | 4130-KVZ-0984 CHB250 | 250 | 500 | 310 |
| 6 | 4130-KVZ-1181 CHB300 | 300 | 600 | 360 |
| 7 | 4130-KVZ-1378 CHB350 | 350 | 700 | 410 |
| 8 | 4130-KVZ-1575 CHB400 | 400 | 800 | 460 |

Note:
the fabrication requirements are as follows:
R—semi-circle, and the tolerance is ±0.015"(0.38 mm);
W—width, the tolerance is ±0.030" (0.76 mm);
H—height, the tolerance is ±0.030" (0.76 mm);
P-K value position line, the tolerance is ±0.001" (0.25 mm);
I-typical test block mark;
45 = typical metal grade;
K = tangent value of angle,
V = sound speed and
Z = zero point;
0118 = 01.18", metal radius, and the unit is 00.00";
CHB = heel test block; and
tri-position: 456 = radius of outer circle 456 mm.

Material of the contrast test block: the technical indexes of the contrast test block should be in line with the requirements of GB/T 11259 and ASTM E428 standards. The principle of the invention is as follows: in order to better ensure precision positioning of horizontality, verticality and sound path for oblique incidence ultrasonic flaw detection of the hollow forged piece in the circumferential direction, a heel test block is designed; and by firstly calibrating the angle of a probe, calculating the ultrasonic reflection sound path S1=30+R×cos (β) and S2=60+R×cos (β) and further calibrating the speed and the zero point of the probe, the precision positioning for oblique incidence detection of the curved surface forged piece is achieved.

The present invention significantly improves the precision positioning of ultrasonic oblique incidence defect detection, greatly improves the ultrasonic circumferential oblique incidence detection level of the curved surface forged pieces, can be simultaneously matched with a series of various heel test blocks with the circular arc radius difference of 50 mm and can further realize accurate positioning of ultrasonic flaw detection against longitudinal defects of the hollow forged pieces. By utilizing the proportion of an instrument calibrated by the heel contrast test block of the invention, the purpose of accurate calibration of the instrument is fulfilled, thereby being more conductive to ultrasonic defect positioning and flaw detection of the curved surface forged pieces.

By utilizing the precision positioning of ultrasonic circumferential oblique defect detection, the positions of the defects in the curved surface forged piece can be effectively determined, thereby being conductive to the fabrication process of judging whether to process or not or judging it as defective in the next process step, and fully realizing the potentials and advantages of the flaw detection method.

The invention claimed is:

1. A heel test block comprising:
a semi-cylinder, a first flat plate and a second flat plate, wherein the side surface of the semi-cylinder comprises a circular arc-shaped surface and a first plane of the semi-cylinder is along the diameter of the semi-cylinder, the first flat plate and the second flat plate are arranged on one side of the first plane, all the parts of the first flat plate have the same thickness, all the parts of the second flat plate have the same thickness, the first flat plate and the second flat plate are arranged in parallel to the first plane, the first flat plate and the second flat plate are arranged on the two sides of a second plane of the semi-cylinder respectively which intersects an axis of the semi-cylinder and is perpendicular to the first plane, and the thickness of the first flat plate is less than that of the second flat plate,
wherein the distance between a plane of the first flat plate, which is parallel to the first plane of the semi-cylinder, and the first plane of the semi-cylinder is the thickness of the first flat plate, and the distance between a plane of the second flat plate, which is parallel to the first plane the semi-cylinder, and the first plane of the semi-cylinder is the thickness of the second flat plate.

2. The heel test block according to claim 1, wherein a third flat plate, wherein all the parts of the third flat plate have the same thickness, the third flat plate is arranged in parallel to the first flat plate, a gap exists between the third flat plate and the first flat plate, and the thickness sum of the first flat plate, the third flat plate and the gap is equivalent to the thickness of the second flat plate.

3. The heel test block according to claim 2, wherein the thickness of the gap is 5 mm±0.5 mm.

4. The heel test block according to claim 1, wherein the thickness of the first flat plate is 30 mm±0.1 mm and the thickness of the second flat plate is 60 mm±0.1 mm.

5. The heel test block according to claim 1, wherein the length of the semi-cylinder and the width of the first flat plate are equivalent to the width of the second flat plate.

6. The heel test block according to claim 1, wherein the upper surface and the lower surfaces of the semi-cylinder are planes, and angle scales are arranged on the upper surface and/or the lower surface.

7. The heel test block according to claim 1, wherein the first flat plate and the second flat plate are cuboids.

8. The heel test block according to claim 7, wherein the radius of the semi-cylinder is R, and the length of each of the first flat plate and the second flat plate is R.

9. The heel test block according to claim 7, wherein the length of the semi-cylinder, the width of the first flat plate and the width of the second flat plate are not less than 25 mm.

* * * * *